United States Patent [19]

Oetjen et al.

[11] 4,019,507

[45] Apr. 26, 1977

[54] PROTECTIVE BREATHING DEVICE HAVING A FILTERING APPARATUS AND ADDITIONAL OXYGEN SUPPLY FOR EMERGENCY USE

[75] Inventors: Georg-Wilhelm Oetjen; Ernst Warncke, both of Lubeck, Germany

[73] Assignee: Drägerwerk Aktiengesellschaft, Germany

[22] Filed: Sept. 24, 1975

[21] Appl. No.: 616,208

[30] Foreign Application Priority Data

Sept. 28, 1974 Germany .......................... 2446410

[52] U.S. Cl. .......................... 128/142 R; 128/142.6

[51] Int. Cl.² ...................... A62B 7/08; A62B 7/10; A61M 16/00

[58] Field of Search ......... 128/142 R, 142.2, 173.1, 128/191 R, 203, 140 R, 209, 210, 142.3, 142.4, 142.6, 142.7, 145 R; 23/281

[56] References Cited

UNITED STATES PATENTS

| | | | |
|---|---|---|---|
| 1,532,654 | 4/1925 | Drager | 128/191 R |
| 2,324,716 | 7/1943 | Nohl | 128/191 R |
| 2,348,074 | 5/1944 | Lambertsen | 128/191 R X |
| 2,695,022 | 11/1954 | Hamilton et al. | 128/191 R |
| 3,202,150 | 8/1965 | Miller | 128/142.2 |
| 3,390,676 | 7/1968 | Warncke et al. | 128/142.2 |
| 3,397,693 | 8/1968 | Warncke | 128/191 R |
| 3,607,122 | 9/1971 | Hwoschinsky | 128/203 X |
| 3,655,346 | 4/1972 | Cotabish | 128/191 R X |
| 3,942,524 | 3/1976 | Yi-Sheng | 128/142 R X |

FOREIGN PATENTS OR APPLICATIONS

| | | | |
|---|---|---|---|
| 461,873 | 6/1928 | Germany | 128/191 |
| 166,813 | 7/1921 | United Kingdom | 128/191 |

*Primary Examiner*—J. Reed Fisher
*Attorney, Agent, or Firm*—McGlew and Tuttle

[57] ABSTRACT

A protective breathing device comprises a housing having a filter therein and with an inlet air passage through the filter and through an internal passage in the housing to a breathing tube having a mouthpiece which is adapted to be fitted to the wearer. The breathing tube includes an exhaling valve for expelling air which is exhaled through the breathing tube. The housing carries an oxygen cartridge which is fired or opened by a firing pin which penetrates the cartridge in order to supply oxygen into the housing passage for flow through the breathing tube when this is necessary. In addition, the housing has an annular chamber surrounding the inhalation duct carrying an economy bag through which portions of the exhaled air may be recirculated for flow back into the breathing tube on a successive respiration in order to maintain the oxygen content within acceptable limits.

5 Claims, 4 Drawing Figures

PROTECTIVE BREATHING DEVICE HAVING A FILTERING APPARATUS AND ADDITIONAL OXYGEN SUPPLY FOR EMERGENCY USE

FIELD AND BACKGROUND OF THE INVENTION

This invention relates in general to the construction of breathing apparatus and, in particular, to a new and useful protective breathing device which is designed as a filtering apparatus with an additional oxygen supply, particularly for use as an escape device.

DESCRIPTION OF THE PRIOR ART

Filtering apparatus are used in breathing protection only in cases where the breathing air supply to the user from the ambience is respirable. This means that the air must be free from toxic matter and, in addition, it must contain oxygen in a sufficient quantity which must not fall below approximately 15%. Toxic matter contained in the air is intercepted in the breathing filter. However, the oxygen lost in the ambient air caused, for example, by a fire or explosion cannot be replaced using such a device.

Protective breathing devices which provide for breathing air supply independently of the ambience are well known. Among them are tube apparatus, reservoir devices and regeneration devices. The tube apparatus limit the freedom of motion. The reservoir and also the regeneration devices are bulky, heavy and complicated in construction. Substantially, they are intended as working devices. Escape devices must be carried along on the body and, in case of need, they must be immediately ready for use.

A known protective breathing device, which is usable as an escape device, comprises a breathing air filter through which the ambient air is taken in as breathing air, and this may be combined with an air or oxygen supply in a pressure gas cylinder. The pressure gas is supplied through a pressure reducer adjusted to a predetermined operating pressure and through an injector into the breathing gas connection and it is inhaled through the connection along with the air from the ambience taken in by the injector. The ambient air flows through the breathing filter which is mounted upstream. While using oxygen as an operating gas for the injector, the user is supplied with breathing air having an increased oxygen content. Thus, the supply with respirable air can be ensured also in an ambience which is wanting in oxygen. A protective breathing device on this principle, however, requires in addition to the pressure gas cylinder, a complicated control equipment in order to obtain a uniform oxygen admixture which is independent of the preliminary pressure. Because of the additional oxygen supply, the relatively simple filtering apparatus becomes complicated, heavier, and therefore, hardly usable for escape. The maintenance in an operational condition is not easy and, in consequence, it is expensive. These drawbacks strongly reduce the possibilities of use of the known protective breathing device.

SUMMARY OF THE INVENTION

This invention is directed to a protective breathing device which operates independently of the state of the ambient air and ensures freedom of movement to the user. It is neither heavy nor complicated in construction, so that it used as an escape device, it can be carried along by the user and rapidly put into operation.

In accordance with the invention, oxygen is developed from a solid oxygen supply stock and is admixed to the breathing air in the inhalation duct downstream of the breathing filter. The solid oxygen supply stock comprises one or more solid oxygen cartridges which are provided with an ignition device. The construction is such that the solid oxygen supply may be added to the inhaled air from the ambience so that the user of the device may be supplied with respirable air under any circumstances. Consequently, the protective breathing device becomes a secure rescue aid for the user even in fires and explosions. The oxygen is admixed automatically. No additional attention on the part of the user is required. The user can concentrate completely on his activity necessary for rescue. The solid oxygen cartridges are small and are structurally connected to the filtering apparatus so that only a small additional space is required. Thus, an essential requirement of an escape device that it be adapted to be easily carried along on a body and, in case of need, used in a trouble-free manner, is met by the inventive arrangement.

In accordance with one aspect of the invention, a flat economizing bag is provided in, and annularly around, the inhalation duct. The bag is enclosed by a cover which conforms to the shape of the housing. In an advantageous manner, during the exhalation phase, the economizing bag is continuously filled with the oxygen which was delivered previously by the solid oxygen supply. During the following inhalation phase, the oxygen is inhaled along with the air. Because of the arrangement, the needed space is minimized. The cover protects the bag against mechanical stressing. The operation of the bag is substantially automatic so that no additional fittings are necessary downstream of the oxygen cartridges.

In a further embodiment of the invention, the protective breathing device is designed as a simple escape device in which the breathed air is conveyed along with the oxygen content to the economizing bag in a simple manner and a check valve is provided on the outlet side of the breathing filter to facilitate this arrangement. To make the device an escape device, instantly ready for use in case of need, it includes an ignition device comprising a spring-loaded firing pin which is suspended between holding plates which are released upon opening of the casing. In the closed state of the casing or the device, the solid oxygen cartridges, along with the pressure piece, are retained by means of a projection provided in the casing device in a position in which the firing pin is locked. The advantage in such a design is that the breathing device becomes instantly ready for use and is placed in an operative position without complicated manipulation. With the opening of the casing, the solid oxygen is ignited and oxygen for admixing to the inhalation air taken from the ambience is instantly available. Thereupon, the oxygen continues to flow without interruption. The simple ignition device does not need any maintenance, and because it is located within the housing, it is exposed to no stressing from the outside. The design, in accordance with the invention, ensures that upon opening of the casing, the firing pin produces its effect in freeing the oxygen for flow through the breathing tube.

Accordingly, it is an object of the invention to provide an improved breathing device which includes a housing having a filter for filtering toxic substances which is connected to inlet means for flow of air from the ambience therethrough and through a breathing tube to a mouthpiece connected to the housing and, wherein, the housing includes an oxygen supply which is connected into a passage between the filter and the breathing tube when there is a need for the oxygen.

A further object of the invention is to provide a breathing apparatus which includes a container having a filter therein with an inlet for the passage of air through a filter which is closed by a check valve through a passage in the housing to a breathing tube having a mouthpiece and wherein the breathing tube has an exhaling valve which is positioned centrally of a connecting duct to an economy bag for holding a portion of the oxygen during the exhalation flow period of the exhaled air and which further includes an oxygen cartridge in the container which is fired to communicate oxygen from the supply thereof to the passage between the filter and the breathing tube.

A further object of the invention is to provide a breathing device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

DESCRIPTION OF THE PREFERRED EMBODIMENT

Figure 1:
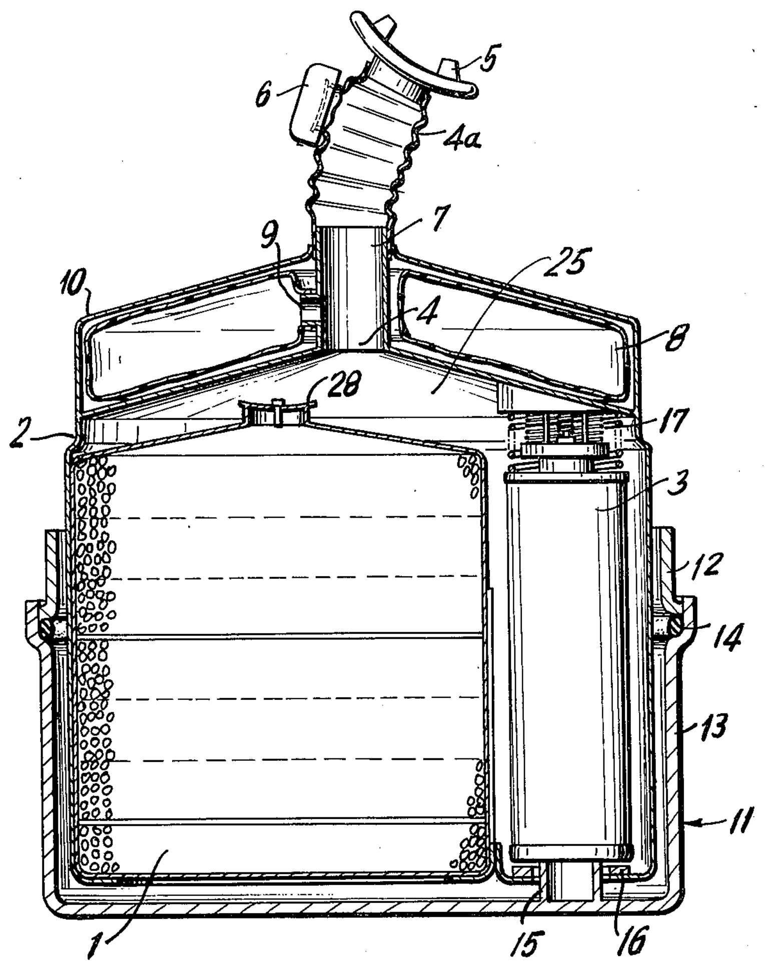
FIG. 1 is a longitudinal sectional view of a protective breathing device constructed in accordance with the invention.
Figure 3:
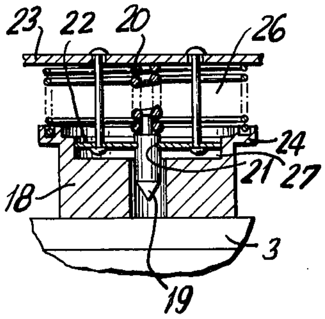
FIG. 3 is an enlarged partial sectional view showing the firing device for the oxygen cartridges.
Figure 4:
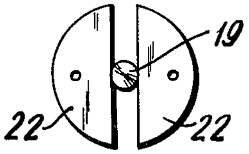
FIG. 4 is a bottom plan view of the holding plates for the firing pin.
Figure 2:
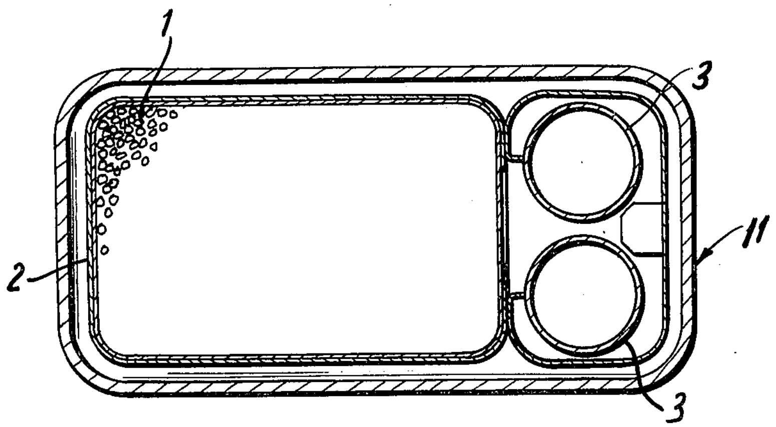
FIG. 2 is a horizontal cross-section of the device shown in FIG. 1.

Referring to the drawing in particular, the invention embodied therein, comprises a protective breathing device which includes a breathing filter 1 for filtering toxic matter including, for example, carbon monoxide. The breathing filter 1 is received within a housing 2 alongside a plurality of solid oxygen cartridges 3, 3, which provide an oxygen supply for use in emergencies. An inhalation duct or tube 4 connects into the top of the housing and it is provided at its outer end with a breathing connection or mouthpiece 5. Instead of a mouthpiece 5, the device 5 may also comprise a complete breathing mask, for example. Breathing tube 5 is also provided with an exhaling valve 6 for the exhalation of air from the mouthpiece back through the breathing tube 4*a* and through the exhaling valve 6. The tubular portion 4*a* connects to an internal inhalation duct 4 within the interior of housing 2 which has a housing fitting or socket at its upper end which connects into the breathing tube 4*a* which is advantageously a flexible bellows or accordion-type fitting.

In accordance with a feature of the invention, an economizing bag 8 is located in an annular chamber formed around the inhalation duct 4 which connects through a connecting passage 9 from the interior of the bag 8 to the inhalation duct 4 and the interior of the inhalation tube 4*a*. The connecting socket 9 also forms a mounting for a mouth portion of the bag which is of annular form. The interior of the housing is provided with a space 25 which communicates with the discharge of the filter 1 and with the inhalation duct and the flexible breathing tube 4*a*. The volume of the bag 8 is approximately 250 $cm^3$. The bag is protected against stressing from the outside by a cover portion 10 of housing 2 which conforms to the configuration of the bag. At a standby condition, the protective breathing device is placed in a casing 11 which comprises a bottom part 13 and a top part 14 of which only the sealing portion of the top part is shown. The two parts of the casing are hermetically connected to each other by means of a sealing ring 14. They are kept connected to each other by an appropriate lock or by an underpressure in the interior of the case 2.

Above the solid oxygen cartridges 3, housing 2 is equipped with an ignition device 26 which causes the ignition of the solid oxygen cartidges 3 automatically upon removal of the top part 12 of the casing. To effect the release of the ignition device 26, cartridges 3 are disposed in housing 2 so as to be movable in the longitudinal direction. However, with the casing of the device closed, they are fixed in an upper position by means of a tubular projection 15 which is provided on the bottom of part 13 of casing 2. In this upper position of cartridge 3, the release mechanism of the ignition device 26 is blocked.

Ignition device 26 comprises a pressure piece 18 which is pressed against the upper edge of cartridges 3 by means of a compression spring 17 which rests on an abutment 23 of housing 2. It also includes a firing pin 19 which is held within a recess 21 of two holding plates 22 with a compression spring 20 in a compressed state. The pin is held by a recess 21 between holding plates 22 which are swingably suspended from an abutment 23. In the blocked position, the holding plates engage laterally against a recess 27 of pressure piece 18. As soon as top part 12 of the casing is removed, housing 2, along with filtering apparatus 1, becomes lifted, relative to the casing part 13 due to the pressure of spring 17 until a sealing 16 provided on the bottom housing 2 comes to apply against cartridges 3. Due to this relative movement of cartridges 3 in a downward relative direction, holding plates 22 disengage from recess 27 and deviate laterally and move over shoulders 24 of pressure piece 18. The firing pin 19 is thereby released and is driven downwardly by spring 20 so that cartridges 3 are ignited. The gaseous oxygen which is developed in cartridges 3 flows through space 25 by housing 2 to the inhalation duct 4 and to economizing bag 8. Breathing filter 1 is provided with a check valve 28 on its outlet side so that the oxygen cannot escape back through the filter.

During inhalation, the oxygen delivered by cartridges 3 mixes with the inhalation air taken in from the ambience and is filtered in breathing filter 1, whereby, the oxygen content is increased.

During the exhalation phase, in which the exhaled air flows downwardly through exhaling valve 6, the oxygen passes through connecting socket 9 into economizing bag 8 and is retained therein until the next cycle in which it is delivered again during the following inhalation. The deformation resistance of the bag 8, together with the flow resistance of connection 9, are smaller than the flow resistance in breathing filter 1.

The burning velocity of solid oxygen cartridges 3 and the volume of economizing bag 8 are dimensioned so that, at every inhalation, the oxygen content of the inhalation air quantity is increased by approximately from 5% to 10%. This is sufficient because even fire gases and explosion fumes contain a residual quantity of oxygen.

While a specific embodiment of the invention has been shown and described in detail to illustrate the application of the principles of the invention, it will be understood that the invention may be embodied otherwise without departing from such principles.

What is claimed is:

1. A protective breathing device, comprising a housing having an upper portion with a breathing duct passage terminating in an outer end having a fitting for breathing by a user, said housing upper portion having an economy chamber therein communicating with said duct, exhaling valve means connected to said duct, said housing including a lower portion with an ambient air inlet opening, a filter positioned over the opening and having an inlet adjacent its lower end communicating with the opening for the passage of ambient air therethrough and also having a discharge adjacent its upper end communicating through said housing to said duct, check valve means in said filter outlet permitting flow only out of said filter outlet, a solid oxygen supply cartridge in said housing lower portion adjacent said filter and having a top end with a discharge communicating with said duct, and firing means connected to said cartridge to effect the liberation of oxygen therefrom out through said cartridge discharge into said duct and into said economy chamber for release through said fitting.

2. A protective breathing device according to claim 1, wherein said breathing duct includes a flexible tube portion, said housing having an annular passage around a portion of said duct in said housing and defining said economy chamber, and an economy bag defining said economy chamber therein connected to said duct.

3. A protective breathing device, according to claim 1, said firing means including an ignition device connected to said solid oxygen supply and comprising a spring-loaded firing pin and means connected to said firing pin for releasing said firing pin to move it into said oxygen supply and cause it to fire and flow into said duct.

4. A protective breathing device, according to claim 3, including projection means in said housing holding said oxygen supply cartridge in a position blocking movement of said firing pin.

5. A protective breathing device, according to claim 3, wherein said housing includes a removable cover and said firing means includes a portion connected to said power and holding said firing pin in a deactivated position and being removable with said cover to release said firing pin.

* * * * *